United States Patent
Ryu et al.

(10) Patent No.: US 11,084,840 B2
(45) Date of Patent: Aug. 10, 2021

(54) METHOD FOR PURIFYING ALLULOSE CONVERSION REACTION PRODUCT

(71) Applicant: SAMYANG CORPORATION, Seoul (KR)

(72) Inventors: Kyung-Hun Ryu, Seongnam-si (KR); Hye Jung Kim, Incheon (KR); Sung Won Park, Yongin-si (KR); Chong Jin Park, Daejeon (KR)

(73) Assignee: SAMYANG CORPORATION, Seoul (KR)

( * ) Notice: Subject to any disclaimer, the term of this patent is extended or adjusted under 35 U.S.C. 154(b) by 0 days.

(21) Appl. No.: 16/461,815

(22) PCT Filed: Nov. 22, 2017

(86) PCT No.: PCT/KR2017/013370
§ 371 (c)(1),
(2) Date: May 17, 2019

(87) PCT Pub. No.: WO2018/124487
PCT Pub. Date: Jul. 5, 2018

(65) Prior Publication Data
US 2019/0315791 A1    Oct. 17, 2019

(30) Foreign Application Priority Data
Dec. 27, 2016  (KR) .................. 10-2016-0180086

(51) Int. Cl.
| | |
|---|---|
| *C07H 1/06* | (2006.01) |
| *B01D 15/18* | (2006.01) |
| *B01D 15/36* | (2006.01) |
| *B01D 25/12* | (2006.01) |
| *B01D 37/02* | (2006.01) |
| *B01J 20/20* | (2006.01) |
| *B01J 20/28* | (2006.01) |
| *C07H 3/02* | (2006.01) |

(52) U.S. Cl.
CPC ............. *C07H 1/06* (2013.01); *B01D 15/185* (2013.01); *B01D 15/362* (2013.01); *B01D 25/12* (2013.01); *B01D 37/02* (2013.01); *B01J 20/20* (2013.01); *B01J 20/28004* (2013.01); *B01J 20/28016* (2013.01); *C07H 3/02* (2013.01)

(58) Field of Classification Search
None
See application file for complete search history.

(56) References Cited

U.S. PATENT DOCUMENTS

| | | | |
|---|---|---|---|
| 2,985,589 A | 5/1961 | Broughton et al. | |
| 3,928,062 A | 12/1975 | Yamauchi | |
| 4,950,332 A | 8/1990 | Stringfield et al. | |

FOREIGN PATENT DOCUMENTS

| | | |
|---|---|---|
| CN | 105431541 | 3/2016 |
| JP | 2008-278794 | 11/2008 |
| JP | 2010-284133 | 12/2010 |
| KR | 10-2011-0108185 | 10/2011 |
| KR | 10-1189640 | 10/2012 |
| KR | 10-1318422 | 10/2013 |
| KR | 10-2014-0021974 | 2/2014 |
| KR | 10-2014-0054997 | 5/2014 |
| KR | 10-2014-0080282 | 6/2014 |
| KR | 10-2014-0143109 | 12/2014 |
| KR | 10-2016-0046143 | 4/2016 |
| KR | 10-2016-0062349 | 6/2016 |
| TW | 201538083 | 10/2015 |

OTHER PUBLICATIONS

Wang, CN 104447888 A, Mar. 25, 2015, machine translation. (Year: 2015).*
Kim, KR 1020160046143 A, Apr. 28, 2016, machine translation. (Year: 2016).*
Yang, KR 1020140143109 A, Dec. 15, 2014, machine translation. (Year: 2014).*
Wong, PLoS One 10(10): eo0141013, 2015. (Year: 2015).*
Beaver Chemicals, How Filteraid Works, internet article published 2012, http://www.filteraid.com/how_filteraid_works.html. (Year: 2012).*
Sigma-Aldrich product page for Celite 500 fine, downloaded from the internet on Sep. 9, 2020. (Year: 2020).*
Okura, JP 2010284133 A, Dec. 24, 2020, machine translation. (Year: 2010).*
Nguyen Van Duc Long et al. "Separation of D-psicose and D-fructose using simulated moving bed chromatography", J. Sep. Sci. vol. 32, pp. 1987-1995, Mar. 2009.
Anonymous, "Granular Activated Carbon (for liquid phase)", Kurary. Retrieved from https://web.archive.org/web/20160304000532/http://www.union-service.jp/item/tks.html.
Anonymous, "Types of activated carbon", Kurary. Retrieved from https://web.archive.org/web/20160817055042/http:/www.kuraray-c.co.jp/activecarbon/about/04.html.
N. Wagner et al., "Multi-objective optimization for the economic production of D-psicose using simulated moving bed chromatography", Journal of Chromatography A, Elsevier. Amsterdam. NL. vol. 1398. Apr. 14, 2015 (Apr. 14, 2015). pp. 47-56. XP029163213. ISSN: 0021-9673. DOI: 10.1016/J.CHROMA.2015.04.008.
EPO, Supplementary European Search Report of EP 17887806.2 dated Aug. 3, 2020.

* cited by examiner

*Primary Examiner* — Layla D Berry
(74) *Attorney, Agent, or Firm* — Lex IP Meister, PLLC

(57) ABSTRACT

The present invention relates to a method of purifying allulose and a method of preparing allulose using the method of purifying, and more specifically the purification method includes mixing allulose conversion product with powdered activated carbon and applying the solid-liquid separation to efficiently remove impurities.

13 Claims, No Drawings

METHOD FOR PURIFYING ALLULOSE CONVERSION REACTION PRODUCT

TECHNICAL FIELD

The present invention relates to a method of purification for allulose and method of preparing allulose by using the purification of allulose, and more specifically, the method of purification for allulose and the method of preparing allulose including steps of reacting powdery activated carbon with a product solution and effectively removing impurities by using solid-liquid separation process.

BACKGROUND ART

Allulose is an epimer of fructose (D-fructose) and is one kind of functional saccharides known as a rare saccharide, and it has been known to have an effect on prevention and improvement of diabetes, since it has sweetness of about 60 to 70% of sugar and almost zero calorie. In addition, allulose is known to have excellent solubility, and it is one of materials where utilization for food is attracting attention.

There are a chemical method and a biological method in the method for preparing psicose, and recently, a method for preparing allulose with a biological method performs allulose conversion reaction by contacting fructose-containing substrate solution with an allulose epimerase or a microorganism producing the enzyme.

However, it is required to separate allulose with high purity, since the reaction solution comprising D-allulose is low purity product. In fact, various methods have been applied to separate industrially produced materials with high purity, and in case of sugar, a product is produced by crystallization after making high purity solution mainly by using a chromatography, to obtain allulose crystals.

In the processes of separation and purification for the allulose, the purification process includes a primary purification step of the activated carbon treatment for adsorbing protein, impurities, etc., decoloring and deodorizing and a secondary purification step of ion purification by using ion exchange resin to remove ionic materials. If the colored components and impurities are not sufficiently removed from the allulose reaction solution before passing through the ion exchange resin, the ion exchange resin is overloaded, the ion exchange is not effectively performed, and the lifetime of the ion exchange resin is shortened. Thus, the activated carbon treatment is very important.

In the conventional activated carbon treatment process, the particle of activated carbon is packed into a column and used for decolorizing allulose conversion liquid. The method has a problem in that a large amount of equipment installation cost and maintenance cost are required. There is a disadvantage in that the activated carbon should be regenerated and reused, and the operation is difficult. When being left for a long time, it has some disadvantages in the reduced adsorption ability and the generation of microorganism. In addition, because of the pressure limit, the processing rate can be slowed when a large amount of sugar solution is discolored the adsorption ability is deteriorated. Also, because of the pressure limit, the processing rate can be reduced, when a large amount of sugar solution is discolored.

Therefore, by differentiating the activated carbon treatment method from the conventional method, it is easier to operate than the prior art and treat a large amount of reaction solution rapidly, thereby making the activated carbon treatment be more efficient and be facilitated for industrial application.

DISCLOSURE

Technical Problem

An embodiment of the present invention is to provide a method of alulose purification for removing target impurities of an alulose product solution using the powdery activated carbon.

Another embodiment of the present invention relates to a method for preparing aluloses comprising an allulose for removing desired impurities of an alulose product solution using the powdery activated carbon.

Technical Solution

The present invention relates to purification of an allulose product solution and removal of fine impure substances, etc. In order to increase the purity of an allulose product solution, there are some problems in low efficiency of removing impurities and the operational troublesome of column packing with the particle of activated carbon. In order to solve the problems, the powdery activated carbon is mixed with allulose conversion product solution, so as to remove the impurities such as the colored components, thereby reducing the operational time and increasing the efficiency of impurities removal higher than the particle of activated carbon.

A method of purifying allulose according to the present invention includes a step of removing impurities of allulose conversion product using a powdery activated carbon, and a method of preparing allulose including the purifying allulose process is provided.

Specifically, in the allulose separation method, the impurity-free product is separated by a simulated moving bed (SMB) chromatography to obtain an allulose fraction and a fructose raffinate, and the allulose fraction may be concentrated into a syrup product or be manufactured into a powder product through a concentration and crystallization process.

In one specific embodiment, the method for preparing allulose comprises (a) a allulose conversion step of preparing psicose-conversion product by performing biological conversion reaction of a fructose-containing raw material; (b) mixing the allulose conversion product with powdery activated carbon; (c) separating the mixture using the solid-liquid separation process to obtain the filtered solution; (d) a allulose separation step of obtaining allulose fraction and fructose raffinate by performing separation with a SMB chromatography of filtered solution; and (e) concentrating or obtaining allulose crystal using the allulose fraction. The solid-liquid separation may be performed by a method such as filtration or centrifugation. The allulose production process according to the present invention can be carried out by a continuous type and a batch type, and preferably a continuous type.

Hereinafter, the method of preparing allulose according to the present invention will be described in detail by each step.

The allulose conversion process is a process for obtaining allulose from the fructose-containing raw material by performing a allulose conversion reaction, and produces a reaction solution including allulose as reaction product converted from fructose.

In one specific embodiment of the present invention, the method for preparing allulose according to a biological method may culture a strain producing allulose epimerase or a recombinant strain including a gene encoding the allulose epimerase and react the allulose epimerase obtained from that with a fructose-containing raw material to produce psicose. The allulose epimerase reaction may be performed in a liquid phase reaction or a solid phase using an immobilization enzyme.

Otherwise, allulose may be produced by obtaining a strain producing allulose epimerase or a recombinant strain including a gene encoding the allulose epimerase, and reacting the fructose-containing raw material with a composition for allulose preparation comprising one or more selected from the group consisting of microbial cell of the strain, culture of the strain, lysate of the strain, and extract of the lysate or culture. When allulose is prepared by using the microbial cell of strain producing the allulose epimerase, it may be performed with a liquid phase reaction or a solid phase using an immobilized microbial cell.

In one specific embodiment of the present invention, the strain producing the allulose epimerase may be the strain which has high stability and can convert fructose to allulose at a high yield or produce the allulose epimerase. The strain may be a strain isolated from nature or its mutant strain, non-GMO strain, or a recombinant strain in which a gene encoding the allulose epimerase is introduced. In one embodiment of the present invention, various known strains as the non-GMO strain may be used. The recombinant strain may be prepared by using various host cells, for example, *E. coli, Bacillus* sp. strain, *Salmonella* sp. strain and *Corynebacterium* sp. strain, etc, but preferably, GRAS strain such as *Corynebacterium* sp. Strain, and may be *Corynebacterium glutaricum*.

The allulose conversion process according to the one embodiment of the present invention is performed by a biological method. For example, in case of solid phase reaction, it may further include a step of packing immobilizede allulose epimerase or microbial cell on a support into a column and a step of providing fructose solution into the packed column. The column being packed by the support-immobilized enzyme or microbial cell and the packing method may be performed according to easily selecting appropriate one by one skilled in the technical field where the present invention belongs according to the used enzyme or microbial cell, or immobilization carrier. In one specific embodiment of the present invention, a packed-bed column may be prepared by packing the immobilized enzyme or microbial cell into a column. An enzymatic reaction, that is, the conversion of fructose to allulose may be performed by providing a substrate of fructose solution to the packed-bed column.

In the conversion reaction of psicose, the reaction may be performed under the condition of pH 4.5 to 7.5, for example, pH 4.7 to 7.0, or pH 5.0 to 6.0 or pH 5.0 to 5.5. In addition, the reaction may be performed under the temperature condition of 30° C. or higher, for example 40° C. or higher. The enzyme activity for converting fructose to allulose (for example, epimerase) can be controlled by a metal ion, and therefore in the production of psicose, the conversion efficiency from fructose to psicose, in the production rate of allulose can be increased, when the metal ion is added. Thus, the composition for producing allulose may further comprise one or more of metal ions selected from the group consisting of copper ion, manganese ion, calcium ion, magnesium ion, zinc ion, nickel ion, cobalt ion, iron ion, aluminum ion, etc.

The detailed technical contents regarding allulose and its preparation method are disclosed in Korean patent publication No. 2014-0021974, Korean patent publication No. 2014-0054997, Korean patent publication No. 2014-0080282, or Korean patent No. 10-1318422.

The fructose as a raw material put into the allulose conversion process according to the present invention may be prepared by a biological method or chemical method, preferably by a biological method. The fructose as a raw material may be provided as a liquid phase raw material, or a powdery raw material such as fructose powder, and in case of fructose syrup, it may be the product obtained in the biological method or chemical preparation method, or one prepared by dissolving fructose powder in a solvent such as water.

The step of removing the impurities in the allulose conversion product according to an embodiment of the present invention may include a treatment process of a powdery activated carbon. The powdered activated carbon treatment can be performed by adding powdered activated carbon to the allulose conversion product, mixing, and filtering. The mixing process may be performed by any method such as stirring. In the activated carbon treatment step, when the reaction solution containing the activated carbon is heated simultaneously by mixing with the reaction solution, the desired colored and fine substances can be effectively removed.

Besides the activated carbon treatment step, the step of removing the impurities may further include at least one step selected from the group consisting of filtration step for removing insoluble matter and an ion purification step.

Since the powdered activated carbon has a high adsorption rate, it can processed the reaction solution with a high purity according to a batch method, there is no problem of microbial generation and deterioration of adsorption ability upon long-term storage, which is a disadvantage of a column packed with granular activated carbon.

The particle size distribution of the powdered activated carbon applicable to the present invention can be appropriately selected in consideration of the impurity removal efficiency and the solid-liquid separation process, and for example, the average particle size may be 10 to 250 micrometers.

In the present invention, the total solid content of the allulose conversion product solution used for the activated carbon treatment is 0.5 to 80% by weight, or preferably 20 to 70% by weight. When the solid content of the product solution is low, it is not efficient to treat the product solution because of a small solid content per the volume to be treated. When the solid content is high, the increased viscosity can makes it difficult to stir, and the removal of impurities, e.g. decolorizing cannot be carried out efficiently because of no uniform spread of the activated carbon.

In an embodiment of the present invention, the amount of the activated carbon added to the allulose conversion product solution is preferably 0.05 to 10% by weight, and more preferably 0.1 to 5.0% by weight, based on 100% by weight of the total solid content of the allulose conversion product solution. If the amount of activated carbon is less, the decolorizing efficiency is lowered.

In an embodiment of the present invention, the temperature of the product solution containing activated carbon may be 30 to 90° C., or preferably 40 to 80° C. The temperature may be determined in consideration of the adsorption capacity and adsorption rate of activated carbon. If the temperature is high, the important component in the product solution may be degraded and browned.

In an embodiment of the present invention, the product solution containing activated carbon may be optionally stirred, and the stirring speed of the solution may be 5 to 500 rpm, or preferably 50 to 300 rpm. The stirring speed can be appropriately selected in consideration of the dispersion degree of the activated carbon and the cost required for stirring, and the utility cost can be not efficiently increased, if the stirring speed is high.

In an embodiment of the present invention, the contact time of the activated carbon with the product solution can be appropriately selected in consideration of the dispersion degree of the activated carbon and the removal efficiency of the impurities, and may be for example, 0.5 to 5 hours or preferably 0.5 to 2 hours. If the contact time is short, the removal of impurities, for example, discoloration may not be sufficiently performed. If the contact time is long, the degradation and browning of the important component may occur.

Then, the product solution containing the activated carbon is subjected to a solid-liquid separation step to obtain a filtered solution, and remove the impurities as filtration residue. The solid-liquid separation step may be performed by a method such as filtration or centrifugation.

In the step of obtaining the filtered solution by performing the solid-liquid separation process for the mixed solution, the solid-liquid separation process separates the solid and the liquid of the mixed liquid, in order to remove the powdery activated carbon with adsorbed impurities. The solid-liquid separation can be carried out by physical separation means such as a passing through of filtration filter or centrifuging.

The passage of the filtration filter can be generally performed by a filtration system process of passing the mixed solution through the filter layer, and preferably by using a filter press. The filter aid of the filtration system may be a fine powder such as diatomaceous earth, pearlite, cellulose, and ion exchange resin. In particular, the pearlite may be used as a filter aid for increasing the filtration efficiency between the filter press plates of pressure addition filter type. The particle size of the filter aid may be 10 to 500 micrometers (um), or preferably 50 to 300 micrometers. If the particle diameter of the used perlite is large, the activated carbon as insoluble material is not completely removed, and the fine activated carbon remains in the reaction liquid to cause turbidity. If the particle diameter is small, the filtration speed is slowed, thereby lowing working efficiency.

In the allulose purification method of the present invention, an ion purification process (e.g., a desalting process) can be performed as an additional process of removing the impurity, after the activated carbon treatment process is performed. The ion purification step in the allulose preparation process is a process for removing ion comprised in psicose-conversion product, and it may be conducted before and/or after SMB chromatography separation step. The primary ion purification which performs ion purification process before conducting the SMB chromatography separation may be carried out by the same or different method with the following secondary ion purification of allulose fraction. For example, it may be performed by using 1, 2 or more separation columns packed with same kind or different kinds of ion exchange resin. The ion purification process may be performed at 35 to 50° C. temperature, for example, 38 to 58° C., considering physical properties of resin used for ion purification and ion purification efficiency.

In one embodiment of the present invention, the product obtained from the impurity treatment process may be subjected to a separation process of an allulose conversion product including a process for separating a simulated moving bed (SMB) chromatograph. The high-purity separation process may be carried out at a temperature of 45 to 70° C., for example, 50 to 65° C.

In a specific example, the allulose conversion product is separated by SMB chromatography separation into an allulose fraction with higher allulose content than the allulose conversion product, and a fructose raffinate, and the allulose fraction is subjected to an allulose concentration process or a crystallization process.

The allulose content of the allulose fraction may be 85% by weight or higher, for example, 85% by weight to 95% (w/w). The fructose raffinate obtained from the high-purity separation step may be 85% by weight or higher, for example, 85% by weight to 98% by weight of fructose content, and preferably 2% by weight or less of allulose content. Among the fructose raffinates, the content of the saccharides including the other disaccharides or higher degree of polymerization except for fructose and glucose is preferably less than 10% by weight. The saccharides including disaccharides or higher degree of polymerization in the impurities may include maltose, isomaltose and the like, and may include maltose-related or isomaltose-related oligosaccharides.

In one embodiment of the present invention, the high purity separation step using SMB chromatography is a separation method useful for securing stability of materials, due to no phase change in the separation process. In these adsorption separation methods, a chromatography separation method has been used in abundance as a liquid phase adsorption separation method. Among them, a simulated moving bed (SMB) adsorption separation method is a separation technology proposed in U.S. Pat. No. 2,985,589 in 1961, and has an advantage that the purity and productivity are excellent and the use of less solvent is possible, compared to the conventional batch chromatography, by continuous separation using many of columns. The simulated moving bed (SMB) adsorption separation process is a process, in which injection of separation target mixture and production of raffinate and extract are implemented continuously. Since a cation exchange resin of strong acid in which a salt is added, which is widely used for a process of monosaccharide separation is used as a separation resin in the SMB, metal ions are comprised in products obtained after performing the separation process. An example of cation exchange resin of strong acid may be a cation exchange resin in which a calcium activated group is attached.

The allulose fraction obtained in the high-purity separation process using SMB chromatography in the allulose preparation process of the present invention may be commercialized as liquid phase syrup through a allulose concentration process, or may be commercialized as allulose crystals through a allulose crystallization process.

The allulose crystallization step comprises a step of secondary ion purification of the allulose fraction obtained in the high purity separation step, a step of concentrating the ion-purified allulose fraction, and a crystallization of the allulose from the concentrate to obtain allulose crystal and allulose crystallization mother liquor. Specific examples of the allulose separation process may include an activated carbon treatment, a primary ion purification, a high-purity chromatographic separation, a secondary ion purification, a concentration and a crystallization process.

It may comprise separation/purification so that the content of allulose in the allulose fraction is 85% by weight or higher, 90% by weight or higher, 91% by weight or higher, 92% by weight or higher, 93% by weight or higher, 94% by weight or higher, or 95% by weight or higher, for example, 85% by weight to 99.9% (w/w).

The allulose purity contained in the allulose crystals may be 90% by weight or higher, 95% by weight or higher, or 99% by weight or higher, and the allulose content in the crystallization mother liquor may be 85% by weight or higher, 90% by weight or higher, 93% by weight or higher, or 95% by weight or higher, for example, 85% by weight to 95% by weight.

The allulose collected by the method of the present invention may be purified and/or crystallized by common methods, and these purification and crystallization belong to common technologies to one skilled in the art. For example, it may be implemented by one or more methods selected from the group consisting of centrifugation, filtration, crystallization, ion exchange chromatography and combinations thereof.

In one embodiment, the secondary ion purification may be conducted for the allulose fraction obtained in the high purity separation process using SMB chromatography, and it may be carried out by the same or different methods with the primary ion purification used in the separation process of psicose.

The method for preparing allulose crystals according to the present invention may comprise a step of concentrating purified allulose solution. The content of allulose in the allulose solution for collecting allulose crystals should be 70% by weight or higher. The purity of allulose in the allulose solution prepared by the allulose epimerase is low as 20 to 30% by weight, so direct crystallization cannot be conducted and a process of purification and concentration up to the desired level should be performed to increase the content of allulose before the crystallization step. In one specific embodiment of the present invention, in order to achieve thermal modification of allulose and desired level of concentration, the concentration may be implemented in the temperature range of 55 to 75° C. The concentration process may be conducted once or twice or more repeatedly until achieving the desired concentration level.

The step of crystallization by cooling may comprise inducing crystal growth by repeatedly conducting temperature rising and cooling, after rapidly cooling in the temperature range of 10 to 25° C. through a heat exchanger.

The method for preparing allulose crystals according to the present invention may further comprise a step of drying after recovering allulose crystals collected in the crystallization step by centrifugation and washing it with deionized water.

Effect of the Invention

According to the present invention, when the target impurities contained in the allulose product solution are treated by batch-type processing of activated carbon in powder form, since the surface area is larger than that of the particulate activated carbon, it is more advantageous for discoloration and removing fine substances, the amount of the treated product solution per unit time is increased, so as to improve the working efficiency.

DETAILED DESCRIPTION OF THE EMBODIMENTS

Hereinafter, the present invention will be described in more detail with the following examples. However, these examples are only for illustrative purpose, and the scope of the present invention is not limited by these examples.'

Example 1. Purification of Allulose Conversion Product (T %=78.6) with Mixing the Activated Carbon Powder 1 L of allulose conversion product (T %=78.6) at a concentration of 50 wt % was prepared in the flask, added with 0.5 wt % of powdery activated carbon based on the solid content and stirred at 75° C., 200 rpm for 1 hour. The powdery activated carbon used of samples 1 to 4 are shown in Table 1 and purchased from Norit activated carbon. Then, the activated carbon was removed by perlite filtration, and T % and turbidity (absorbance at 720 nm) of saccharide sugar solution treated with the activated carbon were measured in order to determine the discoloration and the removal of fine substances. The results are shown in Table 3.

TABLE 1

| Kind of activated carbon | Average diameter |
| --- | --- |
| Sample 1 | 45.4 μm |
| Sample 2 | 44.2 μm |
| Sample 3 | 27.7 μm |
| Sample 4 | 18.5 μm |

Comparative Example 1. Purification of Allulose Conversion Product (T %=78.6) with Mixing the Activated Carbon Particle 1 L of allulose conversion product (T %=78.6) at a concentration of 50 wt % was prepared in the flask, added with 0.5 wt % of powdery activated carbon based on the solid content and stirred at 75° C., 200 rpm for 1 hour. The powdery activated carbon used of samples 1 to 4 are shown in Table 2 and purchased from Norit activated carbon. Then, the activated carbon was removed by perlite filtration, and T % and turbidity (absorbance at 720 nm) of saccharide sugar solution treated with the activated carbon were measured in order to determine the discoloration and the removal of fine substances. The results are shown in Table 3.

TABLE 2

| Kind of activated carbon | Average diameter |
| --- | --- |
| Sample 5 | 1.25 mm |
| Sample 6 | 1.1 mm |

Example 2. Purification of Allulose Conversion Product (T %=70.4) with Mixing the Activated Carbon Powder 1 L of allulose conversion product (T %=70.4) at a concentration of 50 wt % was prepared in the flask, added with 0.5 wt % of powdery activated carbon based on the solid content and stirred at 75° C., 200 rpm for 1 hour. The powdery activated carbon used of samples 1 to 4 are shown in Table 2 and purchased from Norit activated carbon. Then, the activated carbon was removed by perlite filtration, and T % and turbidity (absorbance at 720 nm) of saccharide sugar solution treated with the activated carbon were measured in order to determine the discoloration and the removal of fine substances. The results are shown in Table 4.

Comparative Example 2. Purification of Allulose Conversion Product (T %=70.4) with Mixing the Activated Carbon Particle 1 L of allulose conversion product (T %=70.4) at a concentration of 50 wt % was prepared in the flask, added with 0.5 wt % of powdery activated carbon based on the solid content and stirred at 75° C., 200 rpm for 1 hour. The powdery activated carbon was the same as that of Comparative Example 1 and are shown in Table 2. Then, the activated carbon was removed by perlite filtration, and T % and turbidity (absorbance at 720 nm) of saccharide sugar solution treated with the activated carbon were measured in order to determine the discoloration and the removal of fine substances. The results are shown in Table 4.

Test Example 1. Analysis of T % and Turbidity for Allulose Conversion Product with Mixing the Activated Carbon The T % at 420 nm was measured using a UV spectrophotometer to determine the discoloration level of the allulose product solution treated with activated carbon according to Examples 1 and 2 and Comparative Examples 1 and 2. The sample to be measured had 30 Brix and analyzed using a 1 cm quartz cell. T % means the ratio of transmitted light to incident light. In contrast to absorbance, the value increases as the transmitted light increases. Therefore, the color is lighter and more transparent, as the value is high.

The absorbance (abs) at 720 nm was also measured using a UV Spectrophotometer to determine the level of fine substances. The sample to be measured had a concentration of 30 Brix and analyzed using 1 cm quartz cell. After treating the activated carbon with allulose reaction solution which the initial T % and turbidity of the allulose conversion reaction solution were 78.6 and 0.032, T % and turbidity are analyzed and the result are shown in Table 3.

TABLE 3

| Item | Kind of activated carbon | T % | Turbidity (720 nm) |
|---|---|---|---|
| Example 1 | Sample 1 | 96.1 | 0.003 |
| | Sample 2 | 97.9 | 0.003 |
| | Sample 3 | 98.1 | 0.003 |
| | Sample 4 | 98.4 | 0.002 |
| Comparative Example 1 | Sample 5 | 87.6 | 0.008 |
| | Sample 6 | 92.8 | 0.007 |

After treating the activated carbon with allulose reaction solution which the initial T % and turbidity of the allulose conversion reaction solution were 70.4 and 0.024, T % and turbidity are analyzed and the result are shown in Table 4.

TABLE 4

| Item | Kind of activated carbon | T % | Turbidity (720 nm) |
|---|---|---|---|
| Example 1 | Sample 1 | 93.8 | 0 |
| | Sample 2 | 96.6 | 0 |
| | Sample 3 | 97.0 | 0.001 |
| | Sample 4 | 97.4 | 0 |
| Comparative Example 1 | Sample 5 | 84.2 | 0.006 |
| | Sample 6 | 86.8 | 0.004 |

As shown in Tables 3 and 4, when the activated charbon particles having various average particle sizes were mixed into the allulose reaction solution for purifying allulose, the particle size was the smaller, it was more effective to decolorize and easy to remove fine materials regardless of T % of the initial allulose reaction solution. When the activated carbons were mixed in a batch-type, the activated carbon particles might collide with the activated carbon particles during stirring, resulting in production of additional fine particles. As the powdery activated carbons have a large surface area, they have a large adsorption area with the colored materials and fine particles due to a large surface area, the smaller the amount of the activated carbon, the more effective the decolorization and the removal of the fine particles than the particulate activated carbon.

Comparative Example 3. Relation Between Impurity Removing Efficiency Using a Particle-Packed Column 122 g (250 ml) of the granular activated carbon of the sample 5 shown in Table 4 was filled in the column, and was flowed by the allulose reaction solution (T %=70.4) at a concentration of 50% by weight of allulose. At this time, the temperature of the column was 75° C. and the flow rate was SV 1 (250 ml/60 min=4.17 ml/min), and the pressure applied to the column was 0.04 MPa.

SV refers to a value representing the processing efficiency of the fluid raw material in the continuous flow type reaction apparatus. When F [$m^3$/h] is flow rate of the raw material and VR is inner volume of reaction apparatus, SV [$h^{-1}$] of space velocity is represented by formula of Sv=F/VR. SV means the flow volume of raw material capable of supplying per unit time and unit volume of the reaction apparatus, and represented by unit of 1/h.

As the column speed is the lower, the contact time between the activated carbon and the reaction solution is the longer. Therefore, the removal of the impurities is more efficient at the lower column speed, but the reaction solution treated per hour is decreased. In addition, the the column speed cannot be increased indefinitely and the pressure limit of the column used in the lab is 0.07 Mpa, so the column speed could not be increased any more.

As an experimental result, the treatment efficiency of particle-packed column at various column speeds is shown in Table 5.

TABLE 5

| SV | Pressure (MPa) | Solution amount treated per unit time (ml) | Color index (T %) | turbidity |
|---|---|---|---|---|
| SV 0.5 | 0.03 | 125 | 97.7 | 0 |
| SV 1 | 0.04 | 250 | 95.5 | 0 |
| SV 2 | 0.05 | 500 | 94.4 | 0 |
| SV 3 | 0.06 | 750 | 90.2 | 0 |

The experimental results of Comparative Example 3 using particle-packed column compared to Example 2 using activated carbon powder in a batch-type are shown in Table 6.

TABLE 6

| Item | Granular activated carbon (Comparative Example 3) | Powdered activated carbon (Example 2) |
|---|---|---|
| Amount of activated carbon used per unit time | 122 g | 2.5 g |
| Amount of reaction solution processed per unit time | 750 ml | 1 L |

TABLE 6-continued

| Item | Granular activated carbon (Comparative Example 3) | Powdered activated carbon (Example 2) |
| --- | --- | --- |
| Amount of reaction solution processed per 1 g of activated carbon | 6.15 ml | 400 ml |
| Color index (T %) | 90.2 | 97.4 |
| Turbidity | 0 | 0 |

When a column packed with granular activated carbon is used, the treatment rate of reaction solution is low due to the pressure limit. Therefore, the amount of reaction solution to be treated to the used activated carbon is reduced so as to lower the yield. When the powdered activated carbon is used in a batch-type, the amount of reaction solution to be treated per unit time can be infinitely increased according to the reaction vessel without being affected by the pressure, and a small amount of activated carbon can achieve the large treatment effect.

The invention claimed is:

1. A method of purifying an allulose conversion product, comprising:
    mixing the allulose conversion product with a powdered activated carbon having an average particle diameter of about 10 to about 44 um to produce a mixture, and
    obtaining a filtered solution by removing impurities and the activated carbon with solid-liquid separation for the mixture,
    wherein the solid-liquid separation is performed by passing through a filtering device including filter press and a filter aid having 10 to 500 um of particle size.

2. The method of claim 1, wherein the method of purification further comprises a step of ion purification with a column packed with ion exchange resin, after treating with activated carbon.

3. The method of claim 1, wherein the amount of mixed powdered activated carbon is 0.05 to 10 wt % based on 100 wt % of the total solid content of the allulose conversion product solution.

4. The method of claim 1, wherein the total solid content of the allulose conversion product solution is 0.5 to 80 wt %.

5. The method of claim 1, wherein the mixture solution is at a temperature of 30 to 90° C.

6. The method of claim 1, wherein the filter aid is at least one selected from the group consisting of diatomite, perlite, cellulose and ion exchange resin.

7. The method of claim 1, wherein the mixing the allulose conversion product with a powdered activated carbon is performed by stirring.

8. The method of claim 7, wherein the stirring rate is 5 to 500 rpm.

9. The method of claim 1, wherein the contacting time of allulose conversion product with a powdered activated carbon is 0.5 to 5 hours.

10. A method of preparation for allulose comprising:
    purifying the allulose conversion product to remove impurity, comprising mixing the allulose conversion product with a powdered activated carbon to produce a mixture, and obtaining a filtered solution by removing impurities and the activated carbon with solid-liquid separation for the mixture,
    separating the product with a simulated moving bed (SMB) chromatography to obtain a allulose fraction and a fructose raffinate, and
    concentrating or crystallizing the allulose fraction,
    wherein the solid-liquid separation is performed by passing through a filtering device including filter press and a filter aid having 10 to 500 um of particle size, with the mixture solution, and
    wherein the average particle diameter of powdered activated carbon is about 10 to about 44 um.

11. The method of claim 10, wherein the amount of mixed powdered activated carbon is 0.05 to 10 wt % based on 100 wt % of the total solid content of the allulose conversion product solution.

12. The method of claim 10, wherein the filtering device further comprise a filter aid that is at least one selected from the group consisting of diatomite, perlite, cellulose and ion exchange resin.

13. The method of claim 10, wherein the mixing the allulose conversion product with a powdered activated carbon is performed by stirring.

* * * * *